United States Patent [19]

Veech

[11] Patent Number: 5,200,200
[45] Date of Patent: Apr. 6, 1993

[54] PREPARATION OF ELECTROLYTE SOLUTIONS AND CONTAINERS CONTAINING SAME

[76] Inventor: Richard L. Veech, c/o Laboratory of Metabolism, NIAAA, Room 55A, 12501 Washington Ave., Rockville, Md. 20852

[21] Appl. No.: 509,182

[22] Filed: Apr. 16, 1990

Related U.S. Application Data

[60] Division of Ser. No. 940,331, Dec. 17, 1986, Pat. No. 4,929,449, which is a continuation-in-part of Ser. No. 810,915, Dec. 18, 1985, abandoned.

[51] Int. Cl.⁵ .............................................. A61K 33/14
[52] U.S. Cl. .................................... 424/663; 424/665; 424/678; 424/679; 424/680; 424/681; 424/715; 424/717; 604/7; 604/403; 604/411
[58] Field of Search ............... 424/680, 681, 679, 678, 424/715, 717, 663, 665; 604/7, 403, 411

[56] References Cited

U.S. PATENT DOCUMENTS 3,978,212  8/1976  Barna .................................. 424/717
4,489,535 12/1984  Veltman .............................. 424/717
4,609,372  9/1986  Carmen et al. ...................... 424/533

Primary Examiner—Sam Rosen
Attorney, Agent, or Firm—Hill, Steadman & Simpson

[57] ABSTRACT

Methods are provided for preparing just before administration unit doses of therapeutic solutions which contain redox active unstable and/or diffusable metabolites such as a ketoacid, a sulfhydryl-contining amino acid, or carbon dioxide. The method involves preparing and storing an aqueous solution of stable components which may or may not contain carbon dioxide. A dry powder comprised of unstable components is also prepared and stored separately. These separate component compositions are packaged in, for example, individual chambers of a common scaled container which is so constructed as to permit the opening, by externally applied manual means or the like, of a passageway between such chambers at the time when usage is contemplated. Thus, a fresh solution in desired full dosage form is preparable just befor administration. Improved container structures for practice of this method are also provided.

13 Claims, 2 Drawing Sheets

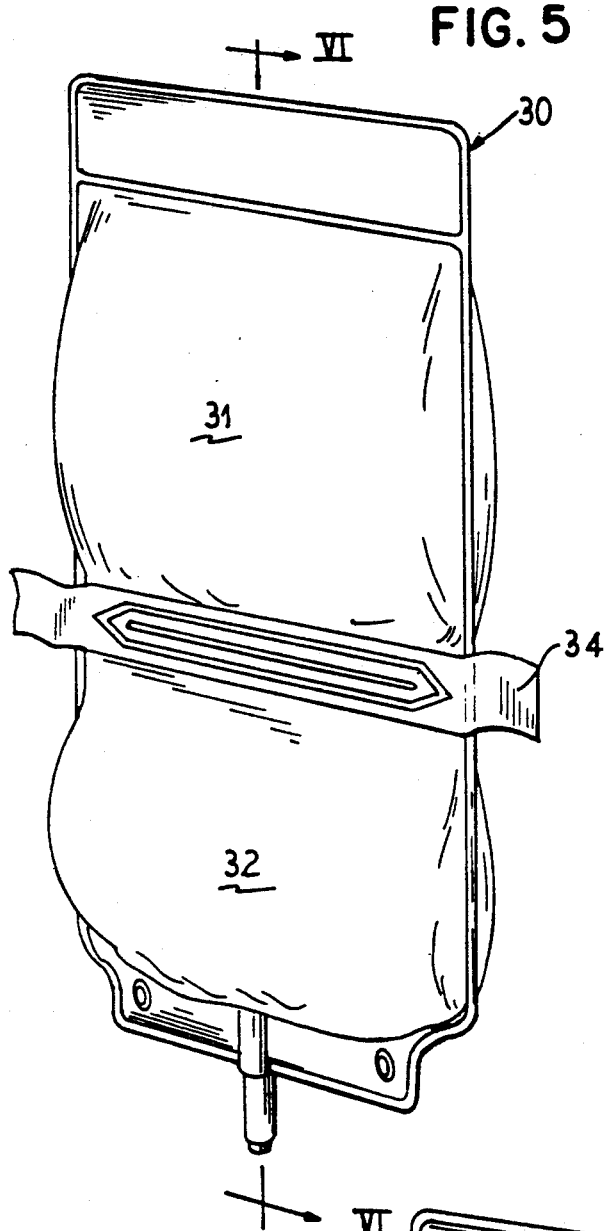
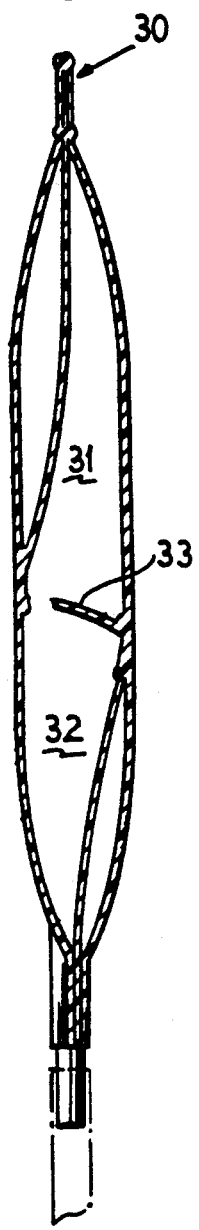
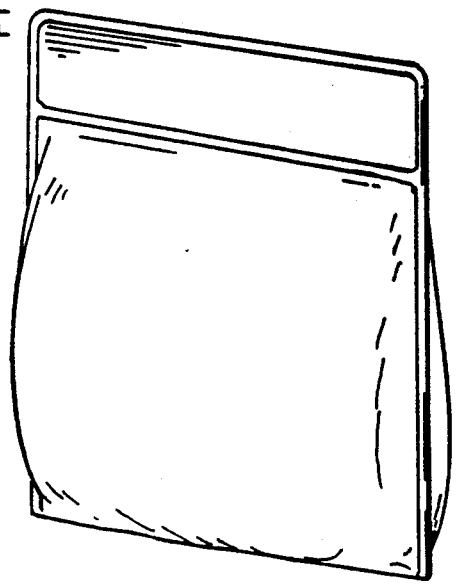
FIG. 5
FIG. 6
FIG. 7

PREPARATION OF ELECTROLYTE SOLUTIONS AND CONTAINERS CONTAINING SAME

This application is a division of Ser. No. 940,331, filed Dec. 17, 1986, now U.S. Pat. No. 4,929,449, which is a continuation-in-part of Ser. No. 810,915, filed Dec. 18, 1985, and now abandoned.

BACKGROUND OF THE INVENTION

1. Field of the Invention

This invention lies in the field of methods for the preparation of therapeutic aqueous solutions which contain dissolved therein at the time of use unstable metabolites of the type normally present in human blood plasma, and also to the field of filled storable containers useful for the storage of such solutions in unit dose forms.

2. Prior Art

Previously, I have provided a family of redox active electrolyte fluid compositions which are useful in therapeutic treatment of mammals and man; see my copending U.S. patent applications identified by Ser. Nos. 747,858, 748,232, 748,184 and 747,792, all filed Jun. 24, 1985, and U.S. patent application Ser. No. 810,918, filed Dec. 18, 1985. The teachings of these applications are incorporated herein by reference.

In addition, I have currently provided parenteral nutrition fluids which contain organic nitrogen compounds, such as amino acids, and the like; see, for example, my concurrently filed U.S. patent application identified by Ser. No. 810,918, filed Dec. 18, 1985.

As those skilled in the art will understand, these fluid compositions employ redox active agents which are in the nature of metabolites and which are normally present in human blood plasma. These agents include (1) metabolizable ketoacid anions which are unstable because of a tendency to decarboxylate and lose carbon dioxide in aqueous solution, (2) metabolizable sulfhydryl amino acids which dimerize and/or oxidize, and (3) dissolved carbon dioxide which escapes from aqueous solutions in which it is dissolved at a concentration above ambient by diffusing into the atmosphere upon standing. As such above referenced other copending applications show, examples of such ketoacid anions include pyruvate, acetoacetate, alpha ketoglutarate, and the like. An example of a sulfhydryl containing amino acid is cysteine.

These characteristics make it very difficult to formulate, package and store fluid systems utilizing these redox active agents. In order to provide dose units of such fluid systems which contain such unstable and/or diffusable metabolites in a substantially non-degraded condition after a period of storage, it is necessary to have storable packaged dose units which can be administered to a patient and wherein the dose unit components are maintainable in a condition equal to a freshly prepared state.

Flexible walled containers incorporating plastics and/or metal foil are currently of growing interest in medical environments and the like. Heretofore, various plastic containers containing integrally a plurality of chambers have been provided for storage of therapeutic materials. Each chamber holds one or a group of separatable components which are admixed into a common solution by chamber wall rupture internally before the solution is used. See, for example, PCT publication number WO85/01268 published Mar. 28, 1985 and references cited therein.

Typically, such plastic containers appear to be formed of materials through which carbon dioxide is diffusable; hence, such containers are not suitable for use with the present invention. So far as is known, no one has heretofore ever faced the problems of formulating unstable and/or diffusable redox active metabolites into therapeutic fluids and of providing plastic containers for storing such formulations. Unless these problems can be simply and reliably solved, particularly so as to provide the capability for achieving storable unit dosages, it may not be possible to use my new fluid compositions on a large scale in human medicine.

Surprisingly and unexpectedly, however, it has now been discovered that simple and reliable methods can be employed to fill certain types of plastic bags with my new fluid compositions, thereby to produce filled containers which are capable of long storage of my solutions and of precursors therefor. Thus, my solutions can be administered to patients even after prolonged storage in an optimum and desired state. Thus, for example, such a container having two or more chambers for the separate storage and selective mixing of two precursor components is now usable in such a way as to produce dispensable dosage units of my solutions.

BRIEF SUMMARY OF THE INVENTION

More particularly, the present invention provides, in one aspect, methods for preparing storable unit doses of therapeutic aqueous solutions which contain dissolved therein at the time of use, redox active unstable or diffusable metabolites of the types normally present in human blood plasma.

For example, one method involves the steps of charging respective first and second compositions into first and second chambers of a plastic container. The chambers are hermetically sealed and the container is itself hermetically sealed. However, the two chambers are internally communicatible with one another while the container is in such sealed condition to achieve solution final preparation under sterile conditions before use.

For another example, a bicarbonate anion containing solution holding dissolved carbon dioxide is charged into a plastic container whose walls are essentially impermeant to carbon dioxide and the container is then sealed for storage before the solution is administered.

In another aspect, the present invention provides new and improved storable filled containers of the sort adapted for the practice of the processes of the present invention.

An object of this invention is to provide methods for administering redox active therapeutic aqueous compositions which methods utilize storable unit dosages.

Another object is to provide a technique for maintaining two precursor components of a single solution separately during storage such that, when the two components are to be used in a combined solution dose form, there is a quick and easy technique for selectively mixing such components together in a closed container system under sterile conditions, thereby to provide a desired dose unit which is adapted for immediate administration.

Another object is to provide a method for repairing a dose unit from two separate components, one of which contains metabolizable ketoacids and/or metabolizable sulfhydryl containing amino acids.

Another object is to provide a method for preparing and storing a dose unit of a therapeutic solution which contains a diffusable redox active component such as dissolved carbon dioxide and which, after storage, can be administered in a sterile condition without appreciable loss of the carbon dioxide.

Another object is to provide classes of filled containers wherein the fill is characterized by containing redox active metabolite agents which are not deteriorated in component structure or concentration by storage before administration.

Other and further aspects, objects, aims, purposes, features, advantages, embodiments, applications, and the like will be apparent to those skilled in the art from the teachings of the present specification taken together with the accompanying drawings.

BRIEF DESCRIPTION OF DRAWINGS

In the drawings:

FIG. 5 is a view similar to FIG. 1, but illustrating a further embodiment of such a container structure;

FIG. 6 is a vertical sectional view taken along the line IV—IV of FIG. 5, but illustrating the compartments of such container in an opened, interconnecting configuration; and FIG. 7 is a side elevational view of a single chambered flexible container adapted for use in the practice of the present invention.

DETAILED DESCRIPTION

Figure 1:
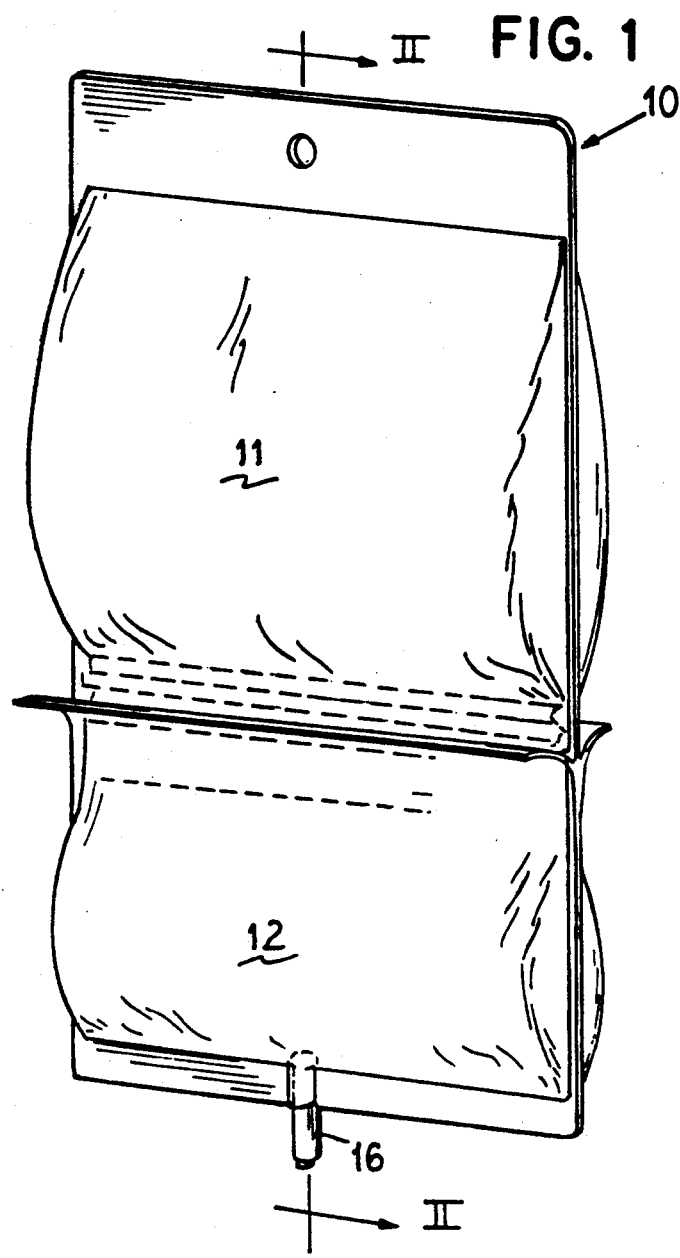
FIG. 1 is a perspective view of one embodiment of a compartmentalized mixing container utilized in the practice of the present invention.
Figure 2:
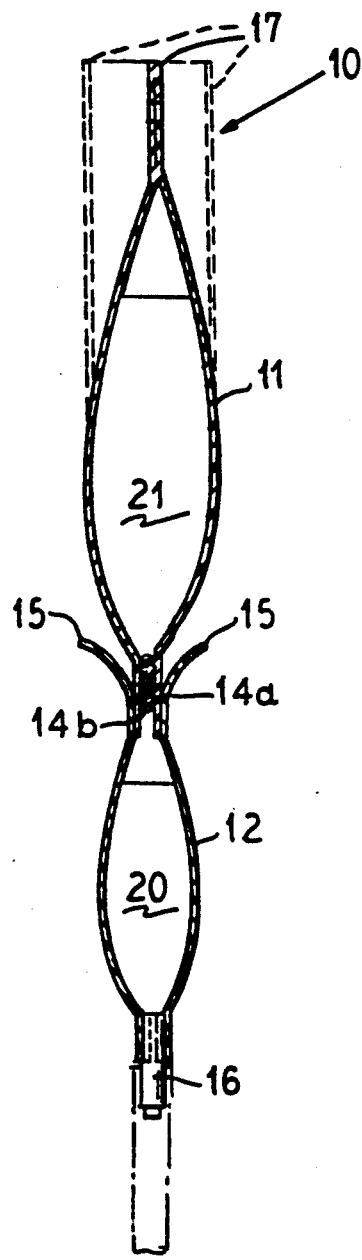
FIG. 2 is a vertical sectional view taken along the line of II—II of FIG. 1.

Referring to FIGS. 1 and 2, there is seen a container 10 having two chambers (a chamber 11 and a chamber 12) for the separate storage and selective mixing of two components. Each chamber 11 and 12 is defined by a pair of sheet members in opposed interfacial relationship to one another with the opposite side edges of the sheet pair defining each chamber 11 and 12 being sealed together.

The bottom edge of the container 11 has mounted therein a pair of mating fastener strips 14A and 14B which are shown, for example, in FIG. 2 in the normally closed configuration wherein the portions 14A and 14B are interengaged with one another in a fluid-tight sealing engagement.

The adjacent wall portions of the container 12 are similarly engaged to outside wall portions of the sheet members defining the chamber 12 with extending tab portions being provided for operating and separating the fastener strip means 14A and 14B from one another.

An alternative structural arrangement, as those skilled in the art will appreciate, can involve using the same sheet members to define each of the chambers 11 and 12, in which event the material comprising the tab portions 15 can be separately laminated in adjacent relationship to the fastener strip means in the general configuration illustrated, for example, in FIG. 2. In a bottommost edge of the chamber 12, a port means is provided, such as a tubular port assembly 16. The port means 16 may be mounted as shown in the container 10 to communicate with the interior of the chamber 12. The tubular port assembly 16 may include a sealing membrane (not shown) capable of being pierced by, for example, the cannula or spike of a parenteral administration set for delivery of the container 10 contents through the administration set to the intravenous system of a patient, or the like, as desired.

The container 10 is initially assembled substantially as shown in FIGS. 1 and 2, but with the top edges 17 of the container left unsealed, and with the fastener means 14A and 14B disengaged (opened). Thus, access is provided to the lower chamber 12. In charging the container 10, a first fill composition 20 is deposited into the lower chamber by way of passing through the region of the upper chamber 11 and through the open fastener strips 14A and 14B. Thereafter, the fastener 14 is closed by externally applied pressure to produce an interlocking, sealing communication between the fastener members 14A and 14B, thereby sealing the fill composition 20 in the chamber 12 in a hermetically isolated condition.

Thereafter, a second fill composition 21, such as an aqueous solution as hereinbelow described, is charged into the upper chamber 11 though the unsealed upper edges 17. The fastener means provides sufficient sealing capacity such that the solution or fill 21 is indefinitely isolated and hermetically sealed in a separate condition from the fill 20 in the container 10 after the top edges 17 have been sealed together. The resulting container with the fills 20 and 21 therein as described is now in a storable condition and may be stored indefinitely until the time of intended use.

When use of the fluid system stored in the container 10 is to be undertaken, the tab portions 15 are manually pulled apart to separate the fastener strips 14A and 14B, thereby permitting the fill 21 to mix with the fill 20. Agitation by shaking or the like of the container 10 after intermixing has occurred aids in obtaining a uniform distribution of the fill 20 with the fill 21. After complete mixing has been achieved, as observed by visual inspection through the walls of the container 10 (when the walls are transparent), the tubular port assembly is engaged by a cannula or spike as hereinabove described, and administration of the contents of the container 10 is undertaken. A convenient and preferred addition for a container 10 is to provide a supporting hole 23 so that the bag 10 can be supported and suspended in the general configuration illustrated, for example, in FIG. 1.

Figure 3:
FIG. 3 is an enlarged fragmentary view of a wall section of the container of FIG. 1.

Shown in FIG. 3 is one form of wall construction. Here, the wall is comprised of a two-layered plastic laminate wherein the inner layer is comprised of ethylene/vinyl acetate, polyvinyl chloride, or the like, while the outer layer is comprised of a material such as saran (polyvinylidene chloride) or other material which is laminatable to the first material. In the situation where the fill in the compartments 11 or 12 of a container 10 is to involve dissolved carbon dioxide gas, it is now preferred to utilize a container structure wherein the inner wall of the container is comprised of a layer of polyethylene terephthalate, or the like, as those skilled in the art will appreciate, or other polymer (resin) which is substantially impervious to carbon dioxide which for example, may be selected from among a variety of plastic materials with a high impermeability to carbon dioxide such as; poly(ureaamides) as cited in Jackson, U.S. Pat. No. 4,596,866, vinylidene chloride and other components as cited in Muruhashi, U.S. Pat. No. 4,393,106, polyisophthalates or poly(ethylene isophthalates) as cited in Smith, U.S. Pat. No. 4,403,090, or similar essentially carbon dioxide impermeant plastic articles of commerce as for example Taira U.S. Pat. No. 4,564,541.

Figure 4:
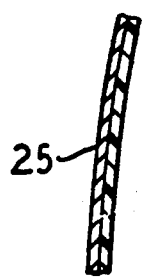
FIG. 4 is similar to FIG. 3, but illustrating an alternative embodiment.

Another wall constructional configuration is illustrated in FIG. 4 where a metal foil 25 comprised of aluminum or the like is heat laminated to an interior layer of an organic polymeric material, such as ethylene/vinyl acetate, an ionomer, or the like, as desired. Multiple layered laminate structures, of course, can be utilized, if desired.

Another bag or container structure adapted for use in the practice of the present invention is illustrated in FIGS. 5 and 6. Such a structure is shown, for example, in Stone et al. U.S. Pat. No. 4,519,499 issued May 28, 1985, the teachings of which are incorporated hereinto by reference. For convenience herein, the container of FIGS. 5 and 6 is designated in its entirety by the numeral 30. The container 30 is provided initially with two separate chambers 31 and 32 which are separated from one another by a diaphragm wall 33. Filling procedures and manufacturing procedures are described in the '499 patent. When use of a charged container 30 is to be undertaken, the pole strip 34 is manually separated from underlying bag surface portions with the result that the tearing action ruptures the diaphragm 33 in regions thereof adjacent to one wall of the container 30 with in turn is adjacent to the strip 34, thereby effectuating an intermixing of the contents of the respective chambers 31 and 32 before administration of the resulting fluid.

Other suitable bags or containers are shown, for example, in Kaufman et al U.S. Pat. No. 4,484,920 and in Corveth U.S. Pat. No. 4,467,588.

In practice, to prepare an aqueous solution containing a redox active unstable ketoacid anion, such as one selected from the group consisting of pyrovate, acetoacetate, and alphaketoglutarate, the sodium, potassium, calcium, or magnesium salts, or the acids of these anions are prepared in a dry, powdered form. When in such form, these dry salts or acids are indefinitely stable in contrast to their behavior when in water solution. These dry salts or acids in a finely divided particulate form are conveniently placed in the chamber provided by Corveth in U.S. Pat. No. 4,467,588 or by Kaufman et al in U.S. Pat. No. 4,484,920, for example, for the powdered component and the chamber is sealed. All other components of the desired aqueous solution are dissolved in water to make a precursor solution which is used as the fill for the liquid chamber in such exemplary containers and then such filled chambers are sealed. In use, the powder holding chamber is opened internally to the liquid holding chamber permitting mixing to be accomplished. When mixing is completed, the resulting solution is a ready for administration to a patient through a desired delivery system. Sterile starting materials, sterile containers and sterile delivery systems are utilized.

For example, in the case of a redox active solution suitable for parenteral therapeutic usage or for parenteral dialysis or for the like, containing dissolved carbon dioxide, the method of the present invention involves the step sequence of first dissolving in sterile and substantially pyrogen free solutes.

Next, the solution is charged (placed) into a bag which is sterile, which has a substantially inert plastic inner wall, and which is substantially impermeable to carbon dioxide. The bag has an internal volume ranging from about 0.5 to 3 liters. The filled bag is then sealed.

After storage and transport of such filled and sealed bag to a location adjacent to a patient to whom the solution is to be administered as a unit dose parenterally or peritoneally, the bag is penetrated with a tubular delivery system associated therewith under sterile conditions. The interior of the bag is interconnected with the patient under sterile conditions through this delivery system.

One class of exemplary solutions for use in such a technique comprises parenteral solutions having the following composition:

| Component | Quantity (in mM/liter) |
|---|---|
| $Na^+$ | 130–165 |
| $K^+$ | 0–5 |
| $Ca^{++}$ | 0–2.5 |
| $Mg^{++}$ | 0–1.5 |
| $Cl^-$ | 90–120 |
| $HCO_3$ | 25–35 |
| $CO_2$ | 1.2–2 |

Another class of exemplary solutions for use in such a technique comprises peritoneal dialysis solutions having the following composition:

| Component | Quantity (in mM/liter) |
|---|---|
| $Na^+$ | 130–165 |
| $K^+$ | 0–5 |
| $Ca^{++}$ | 0–2.5 |
| $Mg^{++}$ | 0–1.5 |
| $Cl^-$ | 90–120 |
| $HCO_3^-$ | 25–35 |
| $CO_2$ | 1.2–2 |
| glucose | 80–250 |

Various other examples of solutions are described in my aforementioned U.S. patent applications. If desired, each of the above classes of solutions can additionally contain, for example, from about 0.1 to 45 mM/liter of l-lactate anions and from about 0.1 to 45 mM/liter of d-betahydroxybutyrate anions.

One preferred class of methods of this invention of this involves the preparation and storage of unit doses of solutions which when prepared for administration containing both of the following
(a) from about 25 to 55 mMoles/Liter of mixture of bicarbonate anions and dissolved $CO_2$ in a millequivalent ratio of 1:1 to 40:1, and
(b) at least one of:
  (1) from about 1 to 55 mMoles/Liter of a mixture of l-lactate anions and pyruvate anion in a millequivalent ratio from about 2:1 to about 20:1, and/or
  (2) from about 1 to 55 mMoles/Liter of a mixture of d-betahydroxybutyrate and acetoacetate anions in a milliequivalent ratio of from about 0.5:1 to 6:1.

One first prepares (1) a precursor aqueous solution which contains the bicarbonate and carbon dioxide and, if employed, the l-lactate and/or d-betahydroxybutyrate, and (2) a dry powder precursor composition which contains a salt, usually sodium, of pyruvate and/or acetoacetate as the case may be.

These respective precursor compositions are packaged in a $CO_2$ impermeant bag, sealed, and stored, using a bag structure as taught herein. Mixing and administration are accomplished.

Steril pure and pyrogen free materials and conditions are used throughout.

EMBODIMENTS

As is apparent from the foregoing specification, the invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

EXAMPLE 1

First a master batch solution is prepared containing the following components in the respected millimoles per liter concentration indicated:

| | |
|---|---|
| $Na^+$ | 124.9 |
| $K^+$ | 4 |
| $Ca^{2+}$ | 1.5 |
| $Mg^{2+}$ | — |
| mEq cations | 132 |
| $Cl^-$ | 96 |
| l-lactate$^-$ | 35.9 |
| d-betahydroxybutyrate$^-$ | — |
| mEq anions | 132 |
| Glucose | — |
| $CO_2$ | 0–0.5 |
| pH | 5.5–6.5 |

Sufficient crystalline sodium pyruvate is measured to provide 5.1 millimoles per liter thereof in a one liter solution of water, and such crystalline material is charged into the chamber 12 of a container as illustrated above in FIGS. 1 and 2. Thereafter, the chamber 12 is sealed and one liter of the solution above prepared is charged into chamber 11 of such container 10 of FIGS. 1 and 2. Thereafter, the chamber 11 is sealed to provide a storage stable container.

Subsequently, the tabs 15 are pulled apart separating the fastener strips 14 from engagement from one another and thereby permitting the solution in chamber 11 to become admixed with the crystalline sodium pyruvate in chamber 12. The crystalline sodium pyruvate readily dissolves in the solution formally contained in chamber 11 so that a single solution results, thereby providing the desired novel redox balanced Ringer's lactate solution which is ready for conventional intravenous administration.

The container 10 here employed has the interior wall portions thereof formed of a layer of polyethylene terephthalate which the outer wall portions are formed of an olefinic polymer such as polyethylene, or the like, as desired. The fabrication of a container such as 10 is known to the prior art.

EXAMPLE 2

A redox balanced bicarbonate peritoneal dialysis solution is prepared as follows:

A bag structure such as illustrated in FIGS. 1 and 2 is prepared which has a two liter volume capacity for chamber 11 thereof.

A master batch solution is prepared containing components as shown below in the respective millimoles per liter concentrations shown:

| | |
|---|---|
| $Na^+$ | 107.9 |
| $K^+$ | 4.5 |
| $Ca^{2+}$ | 1.1 |
| $Mg^{2+}$ | 0.55 |
| mEq cations | 115.7 |
| $Cl^-$ | 102 |
| l-lactate$^-$ | 10.7 |
| d-betahydroxybutyrate$^-$ | 3 |
| mEq anions | 115.7 |
| Glucose | 277 |
| $CO_2$ | 1.45 |
| pH | 5.0 |

A uniform particulate mixture having the following composition is prepared:

| | |
|---|---|
| Particulate $NaHCO_3$: | 58 millimoles |
| Na acetoacetate: | 4 millimoles |
| particulate Na pyruvate: | 3 millimoles. |

The charging procedure employed in Example 1 is repeated and a storable charged bag structure results.

When the tabs 15 are pulled apart, the two liters of solution in chamber 11 intermixes with the particulate solid composition in chamber 12 and solution readily occurs, thereby to provide the desired two liter dialysis solution which is ready for conventional administration.

EXAMPLE 3

An amino acid containing pareteral nutrition solution is prepared as example 2 above with all of the amino acid components except 1-cysteine being placed in the desired concentrations in the master solution. Sufficient dry cysteine-HCl is placed in the smaller compartment of achieve the desired concentration when diluted in the mixture to be administered. The compartment containing the 1-cysteine is ruptured just prior to use, and the solution administered.

I claim:

1. A method for administration of a redox active parenteral therapeutic solution comprising the steps of
(A) dissolving in sterile and substantially pyrogen free water inorganic salts and carbon dioxide which are also both sterile and substantially pyrogen free thereby producing an aqueous solution having the following compositions:

| Component | Quantity (in mMoles/Liter) |
|---|---|
| $Na^+$ | 130–165 |
| $K^+$ | 0–5 |
| $Ca^{++}$ | 0–2.5 |
| $Mg^{++}$ | 0–1.5 |
| $Cl^-$ | 90–120 |
| $HCO_3^-$ | .5–60 |
| $CO_2$ | .1–25 |

(B) filling a sterile bag having a substantially inert plastic inner wall and having an internal volume ranging from about 0.5 to 3 liters with said solution, said bag being further characterized by being substantially impermeable to carbon dioxide,
(C) sealing said bag, (D) storing and moving such resulting sealed bag to a location adjacent a patient to whom said solution is to be administered parenterally, (E) penetrating said bag with a tubular delivery system associated therewith under sterile conditions, and (F) interconnecting the interior of said bag with said patient under sterile conditions through said delivery system.

2. The method of claim 1 wherein said solution additionally contains from about 0.1 to 45 mM of 1-lactate anions.

3. The method of claim 1 wherein said solution additionally contains from about 0.1 to 45 mM of d-betahydroxybutyrate anions.

4. A method for administration of a redox active peritoneal dialysis solution comprising the steps of:

(A) dissolving in sterile and substantially pyrogen free water materials comprising inorganic salts, carbon dioxide and glucose which materials are also both sterile and substantially pyrogen free, thereby to produce an aqueous solution having the following composition:

| Component | Quantity (in mMoles/Liter) |
|---|---|
| $Na^+$ | 130–165 |
| $K^+$ | 0–5 |
| $Ca^{++}$ | 0–2.5 |
| $Mg^{++}$ | 0–1.5 |
| $Cl^-$ | 90–120 |
| $HCO_3^-$ | 25–35 |
| $CO_2$ | 1.2–2 |
| glucose | 80–250, |

(B) filling a sterile bag having a substantially inert plastic inner wall and having an internal volume ranging from about 0.5 to 3 liters with said solution, said bag being further characterized by being substantially impermeable to carbon dioxide, (C) sealing said bag, (D) storing and moving such resulting sealed bag to a location adjacent a patient to whom said solution is to be administered peritoneally, (E) penetrating said bag with a tubular delivery system under sterile conditions, and (F) interconnecting the interior of said bag with the peritoneal cavity of said patient through said tubular delivery system, and (G) transferring under sterile conditions said solution into said peritoneal cavity.

5. The method of claim 4 wherein said solution additionally contains from about 0.1 to 45 mM/liter of 1-lactate ions.

6. The method of claim 4 wherein said solution additionally contains from about 0.1 to 45 mM/liter of d-betahydroxybutyrate anions.

7. An article of manufacture comprised of (A) a sterile sealed bag having a substantially inert plastic inner wall and having an internal volume ranging from about 0.5 to 3 liters, said bag also being substantially impermeable to carbon dioxide, (B) said bag further, being filled with a sterile therapeutic aqueous solution having the following composition:

| Component | Quantity (in mMoles/Liter) |
|---|---|
| $Na^+$ | 130–165 |
| $K^+$ | 0–5 |
| $Ca^{++}$ | 0–2.5 |
| $Mg^{++}$ | 0–1.5 |
| $Cl^-$ | 90–120 |
| $HCO_3^-$ | 25–35 |
| $CO_2$ | 1.2–2 |

8. The article of claim 7 wherein a sterile delivery means including tube is functionally associated with said bag, and which means is adopted for transfer under sterile conditions of said solution from said bag into a patient to whom said solution is to be administered.

9. The article of claim 7 wherein said solution additional contains dissolved therein from about 80 to 250 mM glucose.

10. The article of claim 7 wherein said solution contains additionally at least one anion selected from the group consisting of 1-lactate and d-betahydroxybutyrate.

11. A method for administration of a redox active parenteral therapeutic solution comprising the steps of (A) dissolving in sterile and substantially pyrogen free water inorganic salts and carbon dioxide which are also both sterile and substantially pyrogen free thereby producing an aqueous solution having the following compositions:

| Component | Quantity (in Mmoles/Liter) |
|---|---|
| $Na^+$ | 130–165 |
| $K^+$ | 0–5 |
| $Ca^{++}$ | 0–2.5 |
| $Mg^{++}$ | 0–1.5 |
| $Cl^-$ | 90–120 |
| $HCO_3^-$ | 25–35 |
| $CO_2$ | 1.2–2 |

(B) filling a sterile bag having a substantially inert plastic inner wall and having an internal volume ranging from about 0.5 to 3 liters with said solution, said bag being further characterized by being substantially impermeable to carbon dioxide, (C) sealing said bag, (D) storing and moving such resulting sealed bag to a location adjacent a patient to whom said solution is to be administered parenterally, (E) penetrating said bag with a tubular delivery system associated therewith under sterile conditions, and (F) interconnecting the interior of said with said patient under sterile conditions through said delivery system.

12. A method for administration of a redox active peritoneal dialysis solution comprising the steps of:

(A) dissolving in sterile and substantially pyrogen free water materials comprising inorganic salts, carbon dioxide and glucose which materials are also both sterile and substantially pyrogen free, thereby to produce an aqueous solution having the following composition:

| Component | Quantity (in Mmoles/Liter) |
| --- | --- |
| $Na^+$ | 130-165 |
| $K^+$ | 0-5 |
| $Ca^{++}$ | 0-2.5 |
| $Mg^{++}$ | 0-1.5 |
| $Cl^-$ | 90-120 |
| $HCO_3$ | 25-35 |
| $CO_2$ | 1.2-2 |
| glucose | 80-250, |

(B) filling a sterile bag having a substantially inert plastic inner wall and having an internal volume ranging from about 0.5 to 3 liters with said solution, said bag being further characterized by being substantially impermeable for carbon dioxide, (C) sealing said bag, (D) storing and moving such resulting sealed bag to a location sealed bag to location adjacent a patient to whom said solution is to be administered peritoneally, (E) penetrating said bag with a tubular delivery system under sterile conditions, and (F) interconnecting the interior of said bag with the peritoneal cavity of said patient through said tubular delivery system, and (G) transferring under sterile conditions said solution into said peritoneal cavity.

13. An article of manufacture comprised of (A) a sterile sealed bag having a substantially inert plastic inner wall and having an internal volume ranging from about 0.3 to 3 liters, said bag also being substantially impermeable to carbon dioxide, (B) said bag further being filled with a sterile therapeutic aqueous solution having the following composition:

| Component | Quantity (in Mmoles/Liter) |
| --- | --- |
| $Na^+$ | 130-165 |
| $K^+$ | 0-5 |
| $Ca^{++}$ | 0-2.5 |
| $Mg^{++}$ | 0-1.5 |
| $Cl^-$ | 90-120 |
| $HCO_3-$ | 25-35 |
| $CO_2$ | 1.2-2 |

* * * * *